United States Patent

Koyama et al.

Patent Number: 6,053,936
Date of Patent: Apr. 25, 2000

[54] PORTABLE ILLUMINATION DEVICE FOR MODIFYING CIRCADIAN RHYTHMS

[75] Inventors: Emi Koyama, Osaka; Hozumi Matsubara, Hirakata; Toshio Nakano, Shijonawate; Hiroshi Hagihara, Katano; Akihiro Michimori, Neyagawa, all of Japan

[73] Assignee: Matsushita Electric Works, Ltd., Osaka, Japan

[21] Appl. No.: 08/849,537

[22] PCT Filed: Nov. 26, 1996

[86] PCT No.: PCT/JP96/03460

§ 371 Date: Jun. 23, 1997

§ 102(e) Date: Jun. 23, 1997

[87] PCT Pub. No.: WO97/19720

PCT Pub. Date: Jun. 5, 1997

[30] Foreign Application Priority Data

Nov. 27, 1995 [JP] Japan ................................. 7-308001
Oct. 28, 1996 [JP] Japan ................................. 8-285726

[51] Int. Cl.[7] .................................................. A61N 5/06
[52] U.S. Cl. ............................................ 607/88; 600/27
[58] Field of Search .................. 600/26–27; 607/88–91

[56] References Cited

U.S. PATENT DOCUMENTS

| 5,304,212 | 4/1994 | Czeisler et al. | 607/88 |
| 5,447,527 | 9/1995 | Waldman | 607/88 |
| 5,447,528 | 9/1995 | Gerardo | 607/91 X |
| 5,562,719 | 10/1996 | Lopez-Claros | 607/88 |

FOREIGN PATENT DOCUMENTS

| WO 89/08475 | 9/1989 | WIPO . |
| WO 89/08476 | 9/1989 | WIPO . |
| WO 90/10423 | 9/1990 | WIPO . |
| WO 94/09851 | 5/1994 | WIPO . |

Primary Examiner—Cary O'Connor
Assistant Examiner—Ryan Carter
Attorney, Agent, or Firm—Arent Fox Kintner; Plotkin & Kahn PLLC

[57] ABSTRACT

A portable light treatment device is capable of delivering the illumination which is sufficient in amount but mild to the subject's eyes for assuring effective light treatment without unduly annoying the subject. The device has a surface illuminating unit having an effective surface region of at least 15 $cm^2$ which emits a visible diffused light of reduced luminance variation. The light is selected to give an illuminance of at least 2000 LUX measured at an eye position of the subject. A mount member is provided to mount the surface illuminating unit to a portion adjacent to eyes of the subject to direct the diffused light to the eyes of the subject. Thus arranged portable illumination device has an advantage of delivering sufficient amount of the light to the subject's eyes without dazzling the subject and therefore administering effective treatment without imposing severe restrictions to the subject's daily activities. Preferably, the diffused light is selected to have an average luminance of from 1,000 to 4,000 $cd/m^2$ and have a maximum luminance of less than 6,000 $cd/m^2$ in order to minimize the dazzling effect. Further, the ratio of a maximum to minimum luminance appearing in the effective surface region is selected to be less than 2.5 and difference in luminance between any two points spaced by 2 mm is less than 100 $cd/m^2$ in order to further minimize the dazzling effect.

26 Claims, 13 Drawing Sheets

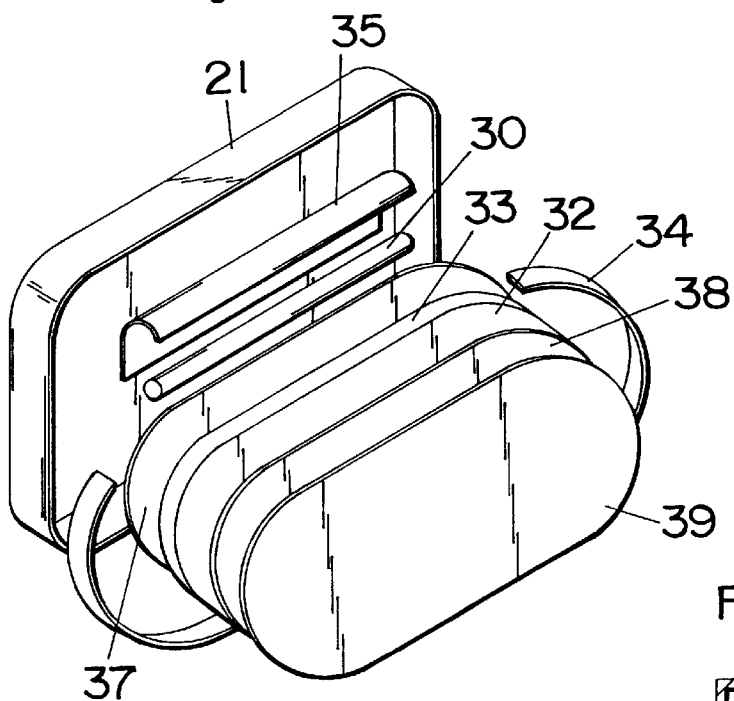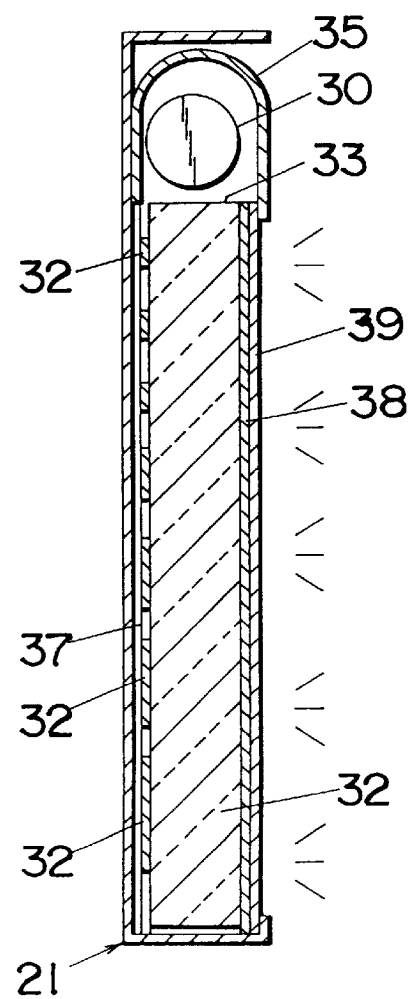

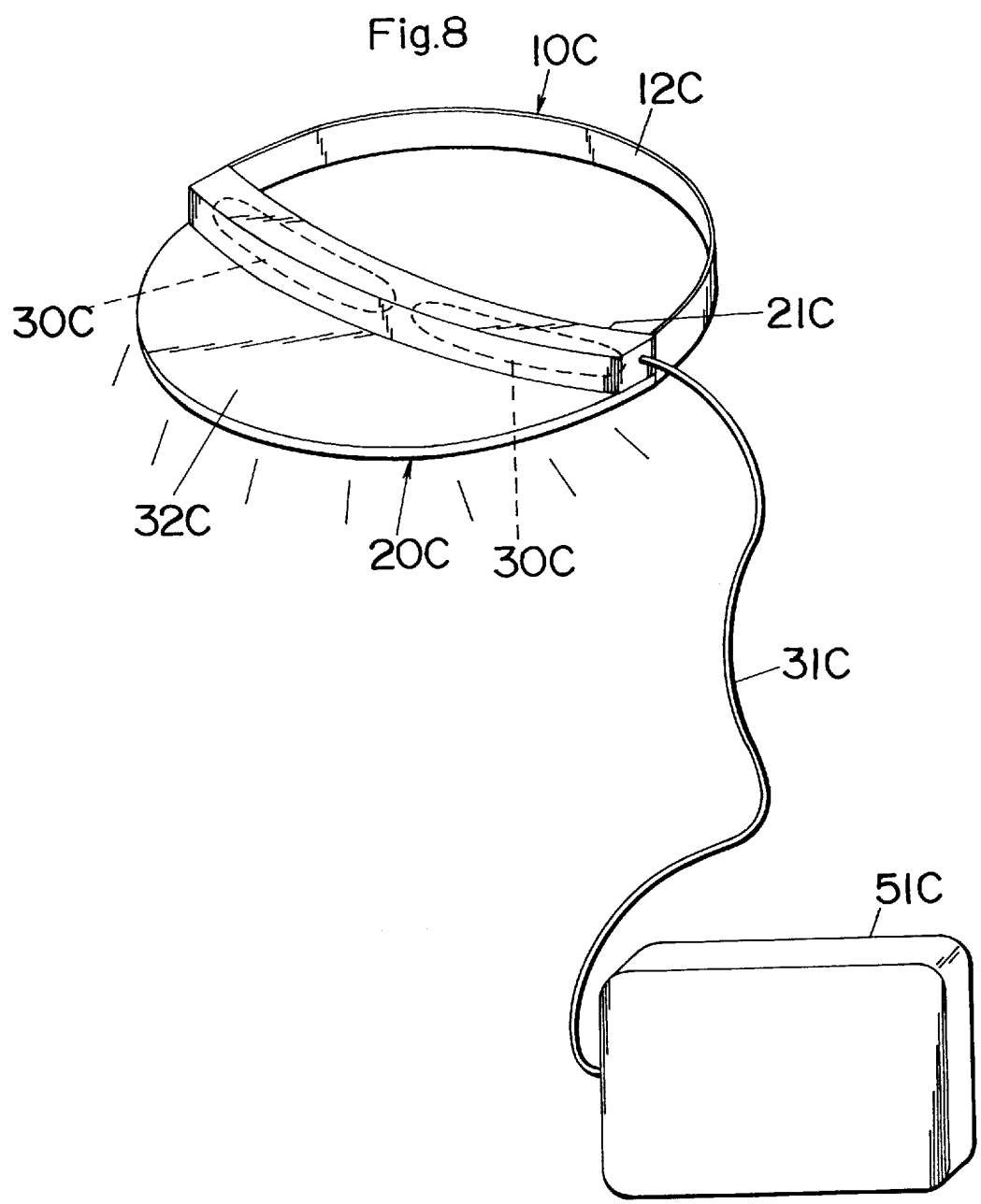

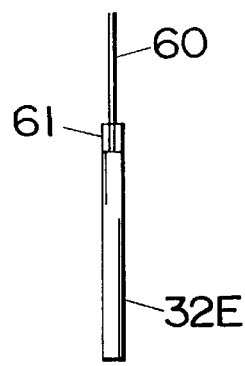
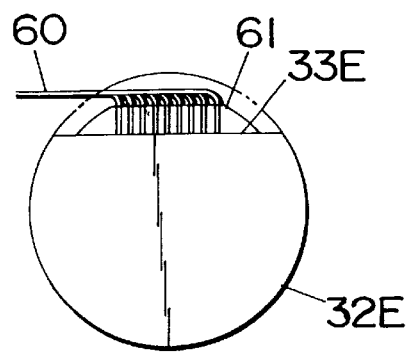
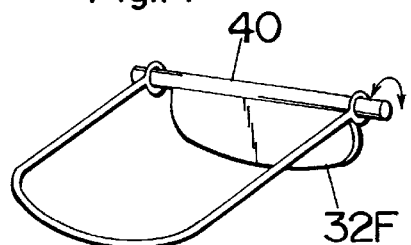
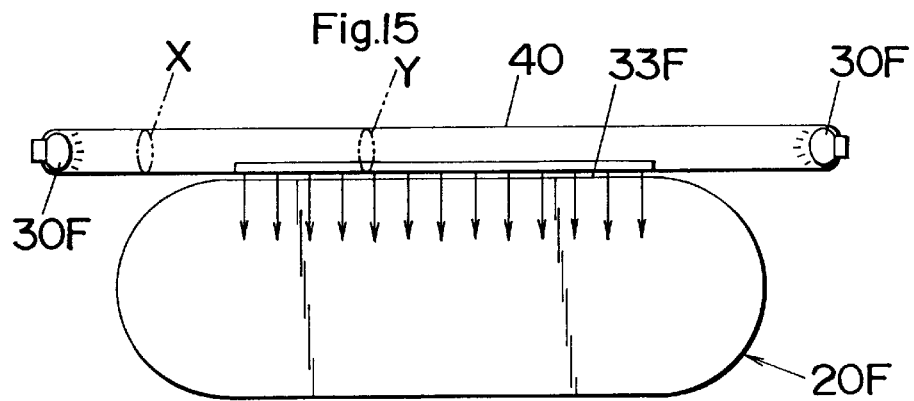
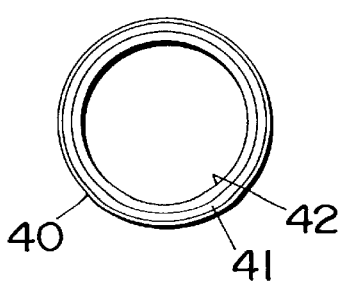
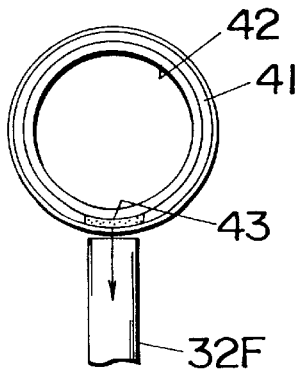

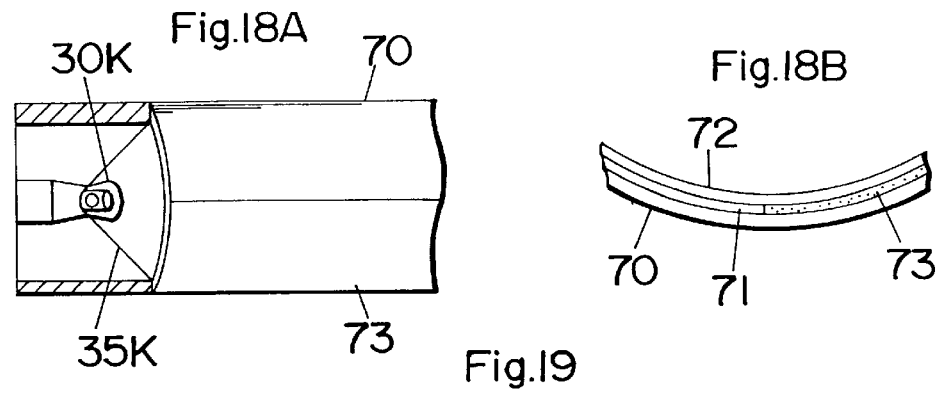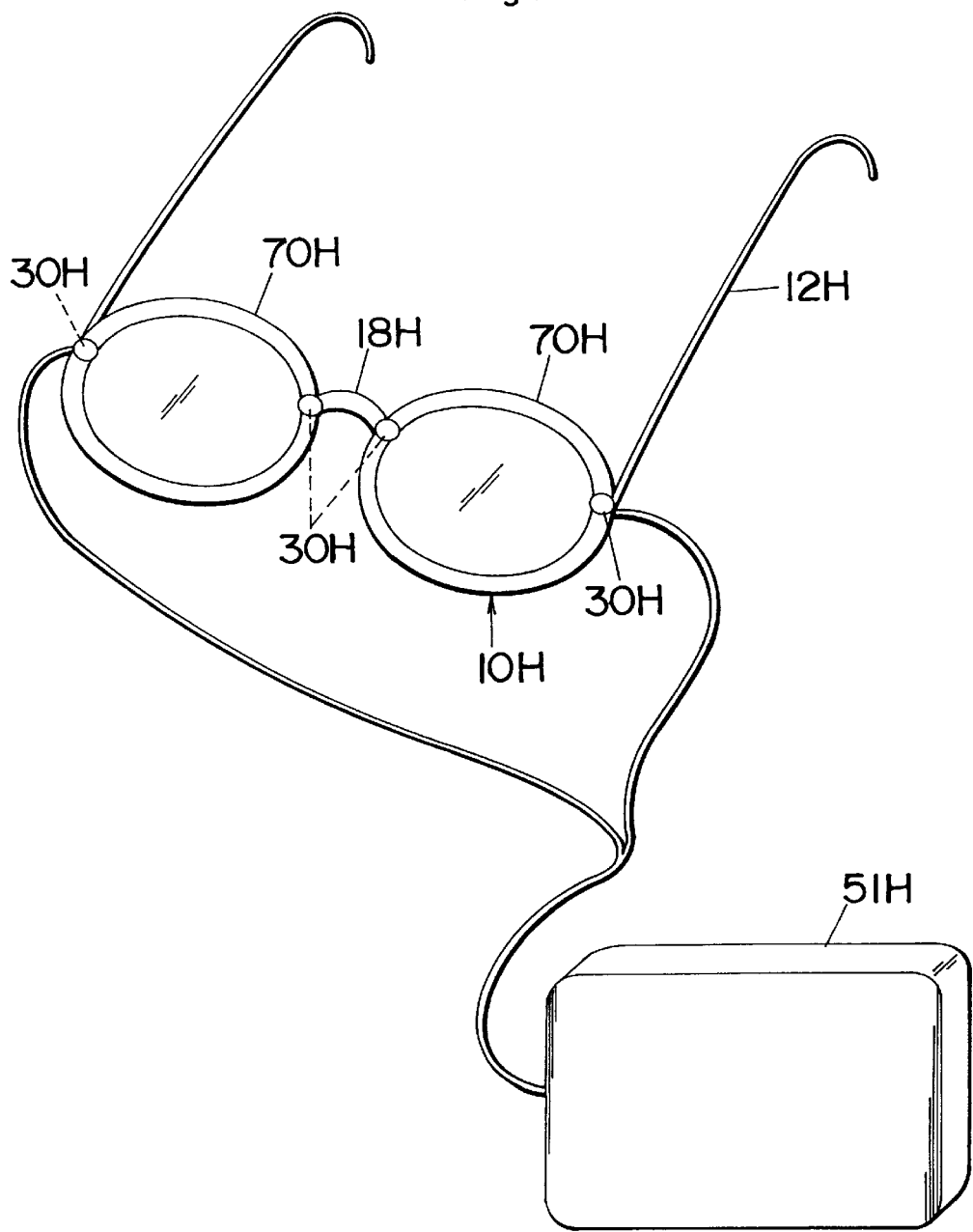

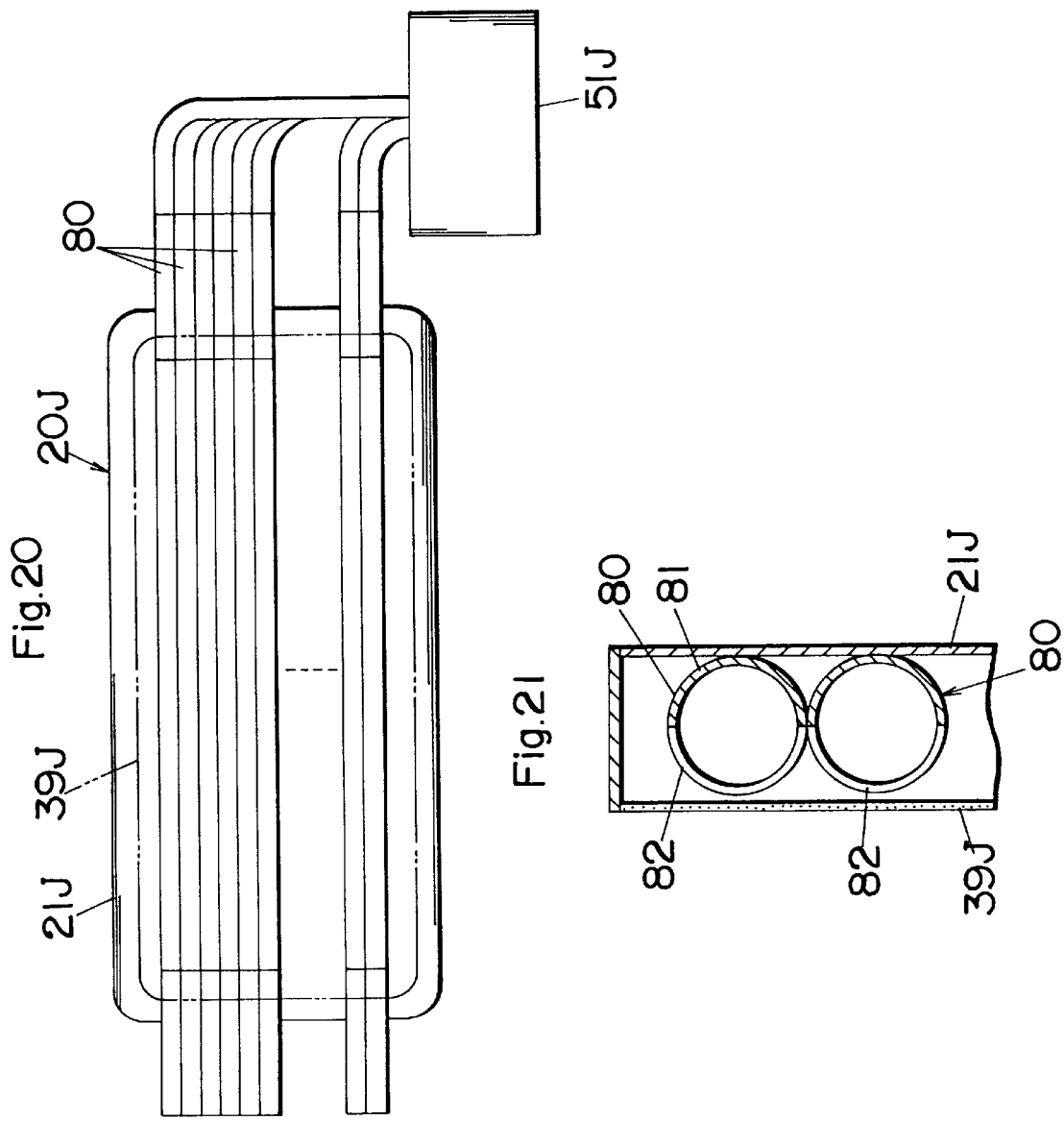

PORTABLE ILLUMINATION DEVICE FOR MODIFYING CIRCADIAN RHYTHMS

BACKGROUND OF THE INVENTION

1. Fields of the Invention

The present invention relates to a portable illumination device for modifying circadian rhythms, and more particularly to such a device which is worn by a subject to direct the light for stimulating the eyes of the subject to the person's eyes to modify biological rhythms and enhance wakefulness.

2. Description of the Prior Art

A bright lighting therapy has been known for treatment of disorders of biological rhythm, i.e. an internal biological clock as well as of sleep and wakefulness cycles. The bright lighting therapy is found effective to treat morbid disorders such as seasonal affective disorders (SAD), endogenous depressions, sleep/wake rhythm disorders, and biological disorders accompanying abnormal behaviors frequently seen in mentally handicapped persons, as well as non-morbid disorders such as jet lag and tiredness associated with shift work.

The bright lighting therapy utilizes a high intensity artificial light source to stimulate the eyes of a subject at a suitable timing for a selected time period in accordance with symptoms of the subject. Due to the requirement of the high intensity light, a device realizing the therapy is normally expected to be bulky and is not suitable for treatment of unserious disorders without disturbing daily activities of the subject. To this end, WO/89/08475, WO/89/08476, and WO/94/09851 propose a portable light illumination device for stimulating neuroendocrine system which is designed to be carried on a subject's body and delivers a high intensity light to eyes of the subject, while permitting the subject to proceed with daily activities during the treatment. However, since this portable device relies on a point or line source of light to produce the high intensity light and the light source is mounted on the bill of a visor to deliver the light directly or indirectly to the subject's eyes, the high intensity light source itself or virtual image thereof will remains in the field of view of the subject to greatly dazzle the subject. With this result, the subject has to narrow one's eye to receive only a reduced amount of light and therefore eventually fail to have effective treatment.

DISCLOSURE OF THE INVENTION

The present invention has been accomplished in view of the above problem to provide an improved portable light treatment device capable of delivering the illumination which is sufficient in amount but mild to the subject's eyes for assuring effective light treatment without annoying the subject. The portable illumination device in accordance with the present invention comprises a surface illuminating unit having an effective surface region of at least 15 cm$^2$ which emits a visible diffused light of reduced luminance variation. The light is selected to give an illuminance of at least 2000 LUX measured at an eye position of the subject. A mount member is provided to mount the surface illuminating unit to a portion adjacent to eyes of the subject to direct the diffused light to the eyes of the subject. Thus arranged portable illumination device has an advantage of delivering sufficient amount of the light to the subject's eyes without dazzling the subject and therefore administering effective treatment without imposing severe restrictions to the subject's daily activities.

Through experiments, it is found effective that the surface illuminating unit gives off the diffused light of which average luminance is elected to be from 1,000 to 4,000 cd/m$^2$ and of which maximum luminance is less than 6,000 cd/m$^2$ in order to minimize the dazzling effect.

Further, it is also found effective that the ratio of a maximum to minimum luminance appearing in the effective surface region is less than 2.5 and difference in luminance between any two points spaced by 2 mm is less than 100 cd/m$^2$ in order to minimize the dazzling effect.

In one embodiment of the present invention, the surface illuminating unit comprises a light conductive element formed with a light inlet for receiving a light from a separate light source and formed to transmit the light therethrough. The light conducting member is provided with a diffuser for diffusing the light emerging from the light conductive member to produce the diffused light directed to the eyes of the subject. By the use of a flexible material as the light conductive member, it is readily possible to conform the surface illuminating unit to the contour of a human face for effectively delivering the light to the subject's eyes and for optimum mounting.

To reduce the weight of the surface illuminating unit, the light conductive element may comprise a light permeable fluid or gel surrounded by a transparent flexible envelop.

One example of the diffuser comprises a flat diffuser plate and a prism sheet disposed between the diffuser plate and the light conductive member. The prism sheet is composed of a transparent sheet integrally molded with a plurality of discrete prism projections arranged in the surface of the sheet in order to orient the light proceeding outwardly of said light conductive member in a fixed direction towards said diffuser plate. Thus, the light passed out of the light conductive element as being directed in various directions can be collected to proceed in the fixed direction before entering the diffuser plate, whereby the light entering the light conductive member can be effectively utilized to give a sufficient illuminance to the subject's eyes.

Preferably, the light conductive element comprises a transparent plate with two opposite major surfaces and an end face defining the light inlet. One of the major surfaces is provided with the diffuser, while the other major surface is provided with a reflector for reflecting the light passing through the light inlet towards the diffuser. With the inclusion of the reflector, the light from the light source can be effectively utilized to give a sufficient illuminance.

The reflector may have either one of a diffuse reflection surface and total internal reflection surface or combination thereof. When the diffusion reflection surface is utilized, it is designed to give a greater amount of reflection at a portion remoter from the light inlet so as to minimize variation in the light intensity along the length of the surface illuminating unit, thereby minimizing the luminance variation of the diffused light as intended.

Further, the reflector may be a dichroic mirror which passes the infrared component of the light while reflecting the light of the other visible components toward the diffuser. Thus, the heat associated with the infrared light from the light source can dissipated away from the subject's face to thereby assure the intended light treatment without suffering from the uncomfortable effect of heat.

The diffuser may be in the form of an opalescent sheet or semi-transparent matted sheet with added delustering characteristic.

In another embodiment, the light conductive element is in the form of a transparent hollow cylinder having one end defining the light inlet. The cylinder is provided with the diffuser around approximately half of its circumference and with a reflector around the remaining approximately half of the circumference for reflecting the light entering the cylinder towards the diffuser. Such cylindrical light conductive element can be attached on a visor or provided with a headband to be readily mounted on the head of the subject to constitute the surface illuminating unit.

The light conductive element may have two opposed end faces each defining the light inlet for receiving the light from each one of two light sources.

In a further embodiment, the light conductive member comprises a plurality of parallel optical fibers with sheathes arranged in a row. One end of each the optical fiber is cooperative to form the inlet section. The optical fibers are stripped of their sheathe at a portion adjacent to the diffuser to give a window or windows through which the light passing through the optical fibers is allowed to be directed outwardly towards and through the diffuser. With the use of the row of the optical fibers as forming the light conductive element, the resulting surface illuminating unit it can be made lightweight sufficient to be comfortably worn by the subject.

Furthermore, the surface illuminating unit may comprises a self-illuminating panel such as composed of electroluminescent material or plasma panel.

In order to position the illuminating member in an optimum position for light treatment to the subjects of different requirements, the mount means includes distance-adjuster for adjusting the distance between the surface illuminating unit and the eyes of the subject, or angle-adjuster for adjusting the angular relation between the surface illuminating unit and the eyes of the subject.

The illuminating device of the present invention includes a controller for controlling to turn on and off the light. The controller is accommodated in a housing which is provided separately from the surface illuminating unit and is designed to be carried on the subject separately therefrom. Thus, the surface illuminating unit can be made lightweight and compact enough to be completely portable even with the controller.

In the case where the light source is held together with the controller for the light source in a housing which is provided separately from the light conductive element, the light conductive member is optically connected to the light source by means of a light guide member such as an optical fiber such that the surface illuminating unit can be made lightweight and compact to a further extent.

The controller includes a timer to turn on and off the light source respectively at preselected start and end times for effective light treatment according to different symptoms of the subjects.

Further, the device may includes a dimmer which varies the intensity of the light emitted from the surface illuminating unit. The dimmer is controlled to increase the intensity of the light gradually in a non-linear relation with respect to time for a period of 5 min. to 30 min. from the start time of energizing the light and until the intensity of the light reaches a predetermined intensity. With this dimming scheme, it is readily possible to start the light treatment consistently with human light adaptation to minimize the fatigue or burden imposed to the subject's eyes.

Preferably, the illumination device utilizes a light sensor which is disposed in the vicinity of the eyes to receive the diffused light from the surface illuminating unit as well as from an environmental light reaching the eyes of the subject so as to provide an output indicative of the total amount of the lights actually delivered to the eyes of the subject over a predetermined period. The dimmer is connected to the light sensor through the controller in order to adjust the intensity of the light from the light source in a feedback manner based upon the output from the light sensor to deliver an effective amount of the light to the eyes of the subject. Thus, a consistent control can be made to give a minimum amount of light sufficient for the light treatment in view of the available environmental light for saving the power requirement.

Alternately, a controller may be made to receive the output from the optical sensor for determining an integrated illuminance of the light and operating to stop generating said light irrespective of the control of said timer upon said integrated illuminance exceeding a predetermined level. Therefore, when the available environmental light is strong enough to add the integrated illuminance over a long time duration, the device can be deenergized even within an expected time duration for saving the power requirement.

The above and other advantageous features of the present invention will become more apparent from the following description of the embodiments when taken in conjunction with the attached drawings.

BRIEF DESCRIPTION OF THE DRAWINGS

FIG. 3A is an exploded perspective view of a surface illuminating unit utilized in the above device;

FIG. 3B is a cross-section of the above surface illuminating unit;

FIG. 8 is a perspective view of a portable illuminating device in accordance with a second embodiment of the present invention;

FIGS. 13A and 13B are respectively front view and side view of a light conductive member of the device of FIG. 11;

FIG. 14 is a perspective view of a portable illuminating device in accordance with a fifth embodiment of the present invention;

FIG. 15 is a front view of a surface illuminating unit of the device of FIG. 14;

FIGS. 16A and 16B are sectional views respectively corresponding to portions X and Y of FIG. 15;

FIG. 18A is a schematic view of a surface illuminating unit of the device of FIG. 17;

FIG. 18B is an enlarged partial sectional view of a hollow cylindrical light conductive member of the device of FIG. 17;

FIG. 19 is a perspective view of a portable illuminating device in accordance with a seventh embodiment of the present invention;

FIG. 20 is a front view of a portable illuminating device in accordance with an eighth embodiment of the present invention;

FIG. 21 is a sectional view of a portion of a surface illuminating unit of the device of FIG. 20;

BEST MODES FOR CARRYING OUT THE INVENTION

First Embodiment

Figure 1:
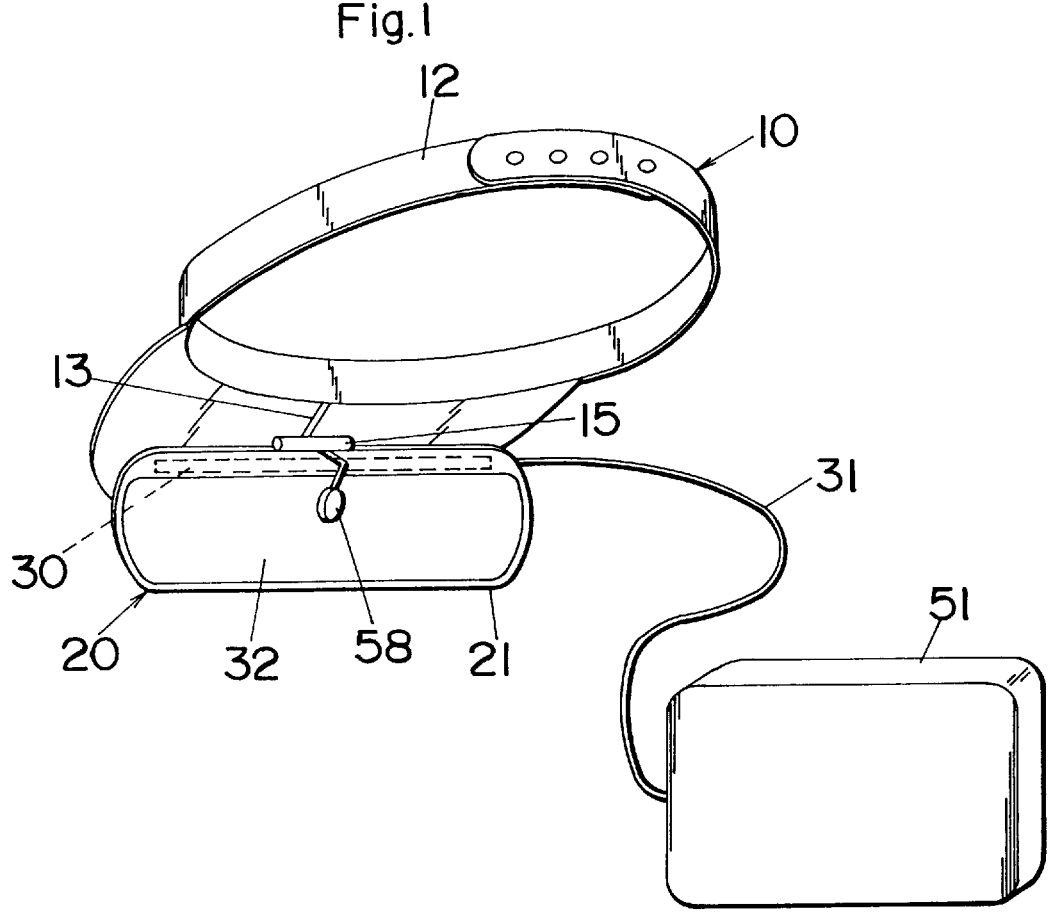
FIG. 1 is a perspective view of a portable illuminating device designed in the form of a visor and viewed from the lower rear of the visor in accordance with a first embodiment of the present invention.
Figure 2:
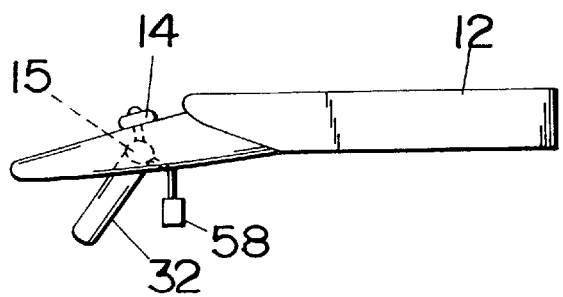
FIG. 2 is a side view of the above device.
Figure 4:
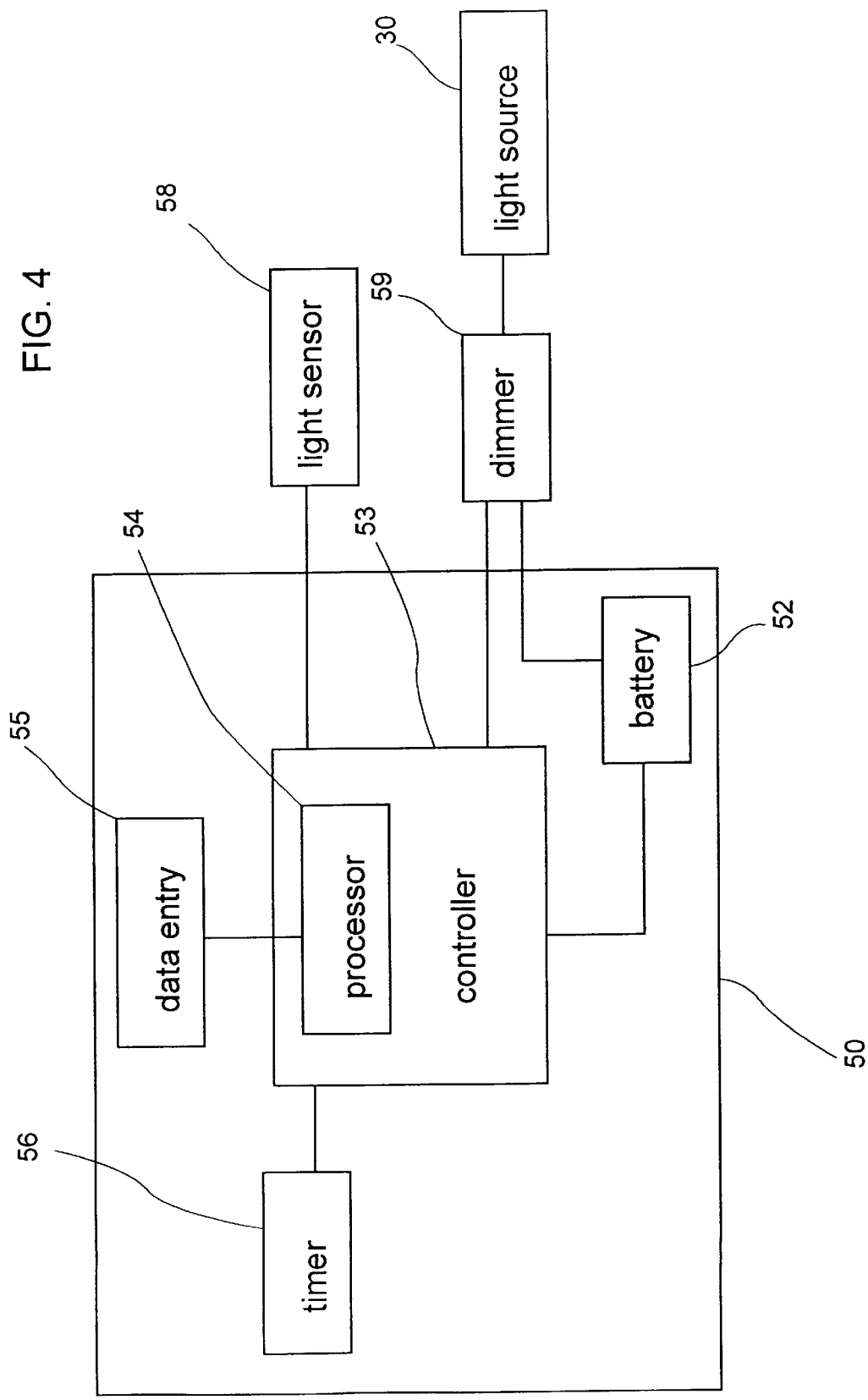
FIG. 4 is a block circuit diagram of a controller system for controlling the above device.

Referring now to FIG. 1, there is shown a portable illumination device in accordance with a first embodiment of the present invention. The device comprises a surface illuminating unit 20 carried on a bill of a visor 10. The visor includes a headband 12 defining a mount member by which the device is worn on the head of a subject to locate the surface illuminating unit 20 in front of the subject's eyes. The surface illuminating unit 20 has a light emitting substantially rectangular surface which emits a visible diffused light to stimulate the subject's eyes for modifying circadian rhythm of the subject. The light emitting substantially rectangular surface has an effective area of about 60 cm$^2$ which radiates the diffused light of substantially uniform luminance as discussed later. The effective area can be made smaller but is revealed through experiments to have at least 15 cm$^2$ in order to stimulate the subject's eyes for treatment of the circadian rhythm disorders. As shown in FIGS. 3A and 3B, the surface illuminating unit 20 comprises a shallow casing 21 accommodating a cold cathode discharge lamp 30 as a light of source and a generally rectangular light conductive plate 32 of acrylic resin which defines a surface source of illumination on its front major surface. The lamp 30 is connected through a cable 31 to a controller housing 51 which accommodates a battery 52 which energizes the lamp 30 as well as a control circuit 50 which controls to turn on and off the lamp 30. The controller housing 51 is provided separately from the illuminating unit 20 to be held in a pocket of clothes or carried in a suitable manner by the subject. As shown in FIG. 4, the control circuit 50 comprises a controller 53 which is connected to a timer 56, a light sensor 58, and a dimmer 59 for controlling to turn on and off the lamp 30 and to dim the same in a manner as will be discussed later. The dimmer 59 is accommodated in the casing 21 of the illuminating unit 20 in an adjacent relation to the lamp 30 and the light sensor 58 is attached to the casing 21 in such a position as to receive the light from the illuminating unit as well as an environmental light directed to the subject's eyes.

As shown in FIGS. 3A and 3B, the light conductive plate 32 is assembled into the casing 21 of which one end face is immediately opposed to the lamp 30 and defines a light inlet 33 extending along the length of the lamp 30 to receive the light therefrom. A reflection tape 34 covers the remaining end and side faces of the plate 32 to avoid the light from passing out of the plate 32. A reflector 35 is also provided to cover the lamp 30 to increase the amount of the light entering the plate 32. Printed on the rear major surface of the light conductive plate 32 is a pattern of diffuse reflection segments 36 of different sizes which are spaced along the length of the plate to give an increasing reflection amount at a portion remoter from the lamp 30 so as to provide uniform distribution of light reaching the front surface of the plate 32 along the length thereof. The light passing rearward through the spaces between the reflection segments 36 is reflected by a reflection sheet 37 which has a total internal reflection surface for reflecting the light towards the front surface of the panel 32. A like reflection surface may be directly formed on the inner surfaces of the casing 21 such as by coating or the like instead of using the reflection sheet 37. Disposed on the front surface of the light conductive plate 32 are a prism sheet 38 and a diffuser sheet 39. The prism sheet 38 comprises a transparent polycarbonate sheet integrally molded on its surface with a plurality of discrete prism projections which act to concentrate the light just emerging out of the plate 32 in various directions to proceed in a fixed directions towards the diffuser sheet 39. The use of the prism sheet 38 can therefore assure an intended relatively high light intensity from the illuminating unit 20 with a reduced requirement on the size and power of the light source. It is this diffuser sheet 39 that gives off the visible diffused light of minimum luminance variation as intended. The diffuser sheet 39 is in the form of an opalescent sheet or a like hazy sheet which may be colored to some extent. Further diffuser sheet 39 may be a semi-transparent matted sheet exhibiting added delustering characteristic.

The light conductive plate 32 and the associated components may be suitable curved in conformity with the human face to deliver the visible diffused light effectively to the subject's eyes. Further, the diffuse reflection segments 36 may be alternately formed on a transparent sheet or the above reflection sheet 37 covering the rear surface of the plate 32 or may be directly formed in the rear surface thereof as minute discrete projections or notches. In addition, the light conductive plate 32 may be formed to have a tapered section in which the thickness thereof is smaller towards the end opposite to the light inlet 33 than at the light inlet.

The surface illuminating unit 20 is designed such that the eye position normally expected to be apart by 2 cm to 6 cm from the unit receives the diffused visible light of at least 2,000 LUX, preferably 3,000 LUX or more in order to effectively modify the circadian rhythm. Further, in order to avoid the subject from being dazzled, the diffused light from the surface illuminating unit 20 is selected to have an average luminance of 4,000 cd/m$^2$ or less and a maximum luminance of less than 6,000 cd/m$^2$. In consideration of the practical limitation that the illumination unit 20 have to be spaced from the eyes by a distance of at least 2 cm and of the required illuminance of at least 2,000 LUX received at the eyes, it was determined experimentally that average luminance of at least 1,000 cd/m$^2$ is necessary to give the required illuminance to the eyes spaced by 2 cm to 6 cm from the surface illuminating unit 20 having the effective illumination surface area of at least 15 cm$^2$. In order to further minimize the dazzling, a study was concentrated on an overall luminance variation as well as a local luminance variation which are expected to cause the dazzling singly or in combination. Through investigations, it was revealed that the overall luminance variation causing no apparent dazzling should satisfy the ratio of a maximum to minimum luminance appearing in the effective surface region being less than 2.5 and that the local luminance variation causing no apparent dazzling should satisfy the luminance difference between any two points spaced by 2 mm in the effective surface region being less than 100 cd/m². With the use of the diffused light of thus selected levels, the subject can be treated by relatively mild light free from suffering undue burden to the eyes.

The surface illuminating unit 20 is attached to the bill of the visor 10 by means of a joint 14 which is slidably engaged in a slit 13 in the bill so as to adjust the distance between the surface illuminating unit 20 and the subject's eyes. The joint 14 includes a hinge 15 which varies the angle of the illuminating unit 20 with respect to the eyes. With these distance and angle adjusting capabilities, the surface illumination unit 20 can be set into an optimum position. The light sensor 58 is also supported to the joint 14.

The timer 56 in the control circuit 50 sets start and end times of turning on and off the lamp 30 and provides an output indicative of the start and end times to the controller 53 which responds to turn on and off the lamp 30 at the selected time. In order to alleviate the jet lag, the controller 53 includes a processor 54 which calculates the start time and end time based upon an departure date/time and place and a destination date/time and place entered at an data entry 55. The controller 53 then responds to control to turn on and off the lamp at the thus calculated start and end times. With this result, a user not familiar with specific knowledge about the biological rhythm can easily to treat the jet lag. Alternately, the timer may be made to simply determine the duration of turning on the lamp 30.

Figure 5A:
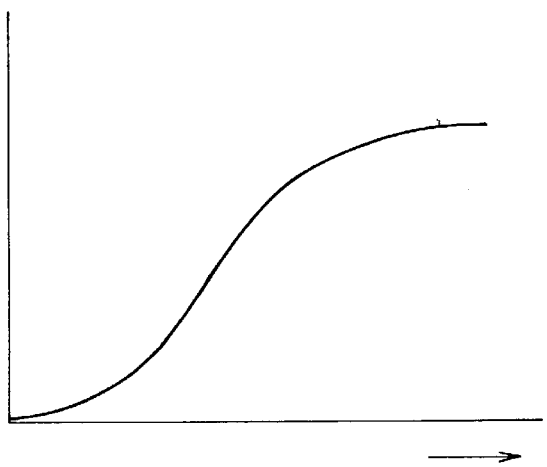
FIGS. 5A and 5B are respectively graphs illustrating manners of gradually increasing illumination level or the light intensity of the surface illuminating unit at the start of operating the device.
Figure 5B:
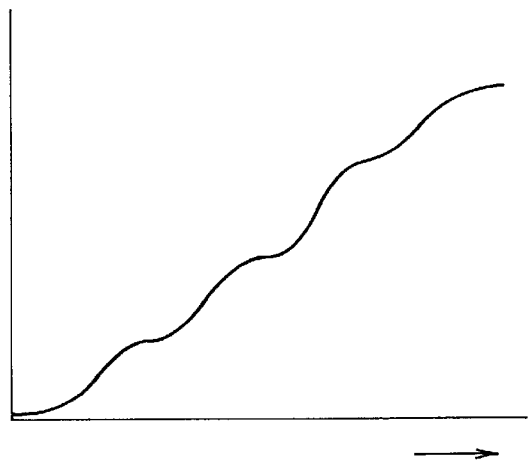

The dimmer 59 is provided to gradually increase the light intensity immediately after the start time in order to start the light treatment in consistent with human light adaptation and therefore minimize fatigue or burden imposed on the subject's eyes. To be well compatible with the human light adaptation, it is set to gradually increase the light intensity in a non-linear relation such as along a generally logarithmic curve as shown in FIG. 5A or a stepped curve as shown in FIG. 5B over a relatively long period of 5 min. to 30 min., preferably about 10 min, before reaching an intended target light intensity. In addition, the dimmer 59 is responsible for gradually decrease the light intensity in the like or other manner before turning off the lamp 30. Further, the dimmer 59 may be utilized to adjust the target light intensity in consideration of the preference and visual characteristic of the subject.

The controller 53 is added another function of controlling the illuminance level incident upon the eyes in a feedback manner by the use of the light sensor 58. For this purpose, the controller 53 includes a circuit which obtains from the output of the light sensor 58 an average illuminance or the integrated illuminance over a short time period, for example, 5 sec. to 30 sec. and compares thus obtained illuminance with the predetermined level from time to time so as to adjust the light intensity in a feedback manner for keeping the predetermined level. As described hereinbefore, the light sensor 58 is arranged to receive the environmental light available to the eyes, in addition to the light from the surface illuminating unit 20, the above feedback control is useful to save the power requirement when the available environmental light is strong.

Alternatively or in addition to the above feedback control, the controller 53 is made to have another function of controlling to stop energizing the lamp 30 irrespective of the control of the timer 56 when the integrated or cumulative amount of the sum of the light from the surface illumination unit 20 and the environmental light exceeds a predetermined level. For this purpose, the controller 53 includes an integrator (not shown) which gives the integrated illumination amount from the output of the light sensor 58 from the start of energizing the lamp. Upon the resulting integrated illumination amount exceeds the predetermined level that is sufficient for the intended treatment, the controller 53 responds to stop energizing the lamp 30 even before the end time determined by the timer 56, thereby saving the power as well as for making the subject free for other activities.

Figure 6:
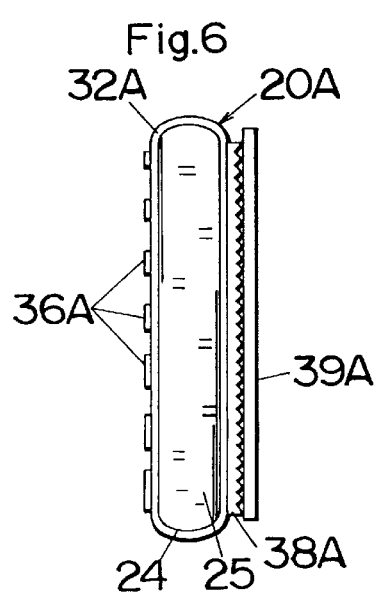
FIG. 6 is a sectional view of a light guide member which may be utilized in the above surface illuminating unit.

FIG. 6 illustrates a modified surface illumination unit 20A with a particular light conductive member 32A which may be utilized instead of the light conductive plate 32 of the first embodiment. The light conductive member 32A is shaped into a flat configuration and comprises a flexible transparent envelop 24 surrounding a light permeable gel or fluid 25 having a light permeability of 80% or more and a refractive index of at least 1.3 such as ethanol, glycerin, paraffin oil, cedar oil, silicone oil, and water.

Like diffuse reflection segments 36A, prism sheet 38A, and diffuser sheet 39A are provided on the rear and front surfaces of the member 32A. The use of the light conductive member 32A is advantageous to easily make the surface illuminating unit flexible sufficient to be curved to any desired shape as well as to have increased impact strength. Although not shown in the figure, the surface illuminating unit may utilizes a stack of transparent sheets or plates as a like light conductive member.

Figure 7:
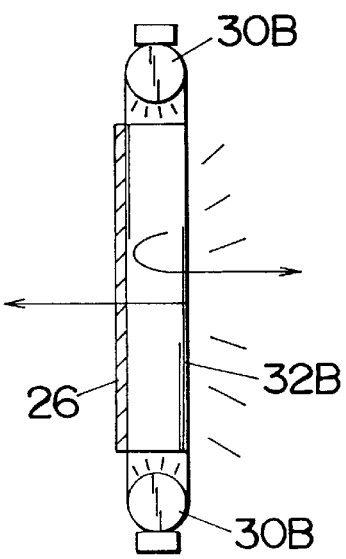
FIG. 7 is a sectional view of a modified surface illuminating unit which may be applied to the above embodiment.

FIG. 7 illustrates another modified illumination unit 20B with two separate lamps 30B on opposite ends of a like light conductive plate 32B and with dichroic mirror 26. The dichroic mirror 26 covers the rear surface of the plate 32B instead of the reflection sheet or segment to allow the infrared component of the light from the lamps 30B to pass but reflects the other visible components of the light towards a like diffuser sheet (not shown) on front of the plate 32B to give a sufficient light intensity. With the use of the dichroic mirror 26, the subject can be free from unpleasant heat associated with the lamp during the treatment.

Second Embodiment

FIG. 8 illustrates a portable illumination device in accordance with a second embodiment of the present invention. The device takes the form of a visor 10 with a headband 12C and comprises a like light conductive panel 32C defining the whole bill of the visor 10C. Formed along a curved rear periphery of the bill or the panel 32C is a casing 21C which accommodates therein two elongated lamps 30C emitting the light into the panel 32C through a light inlet on the rear periphery of the light conductive panel 32C. The panel 32C is formed on its upper surface with a combination of the like reflection sheet 37C and diffuse reflection segments (not shown) as utilized in the first embodiment for reflecting the light entering the panel 32C towards a like diffuser sheet (not seen) formed on the entire lower surface of the panel 32C to constitutes a surface illuminating unit 20C for radiating the diffused visible light to the eyes of the subject wearing the visor. A like controller housing 51C is provided separately from the visor 10C and includes a control circuit of the like configuration as shown in FIG. 4 to effect the like control. Extending from the controller housing 51C is a cable 31C for energizing the lamps 30C in the visor 10C.

Third Embodiment

Figure 10:
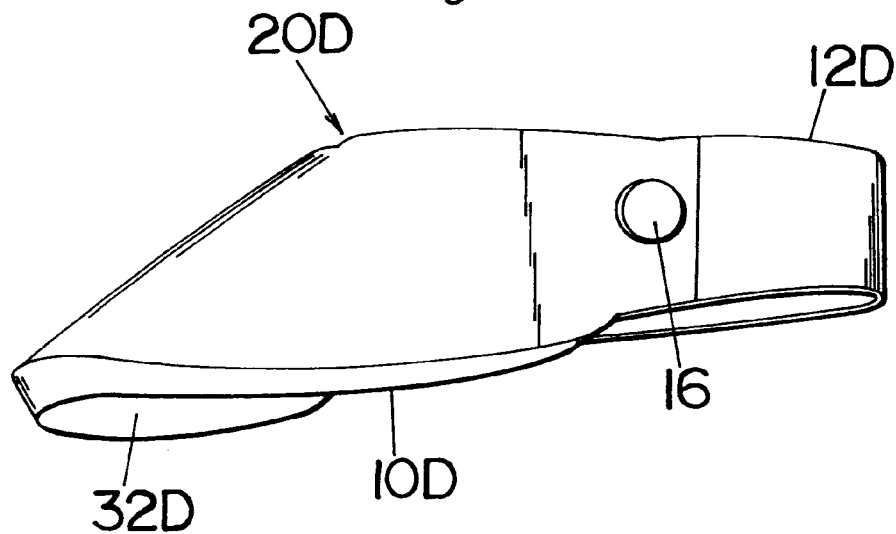
FIGS. 9 and 10 are perspective views of a portable illuminating device in accordance with a third embodiment of the present invention.
Figure 9:
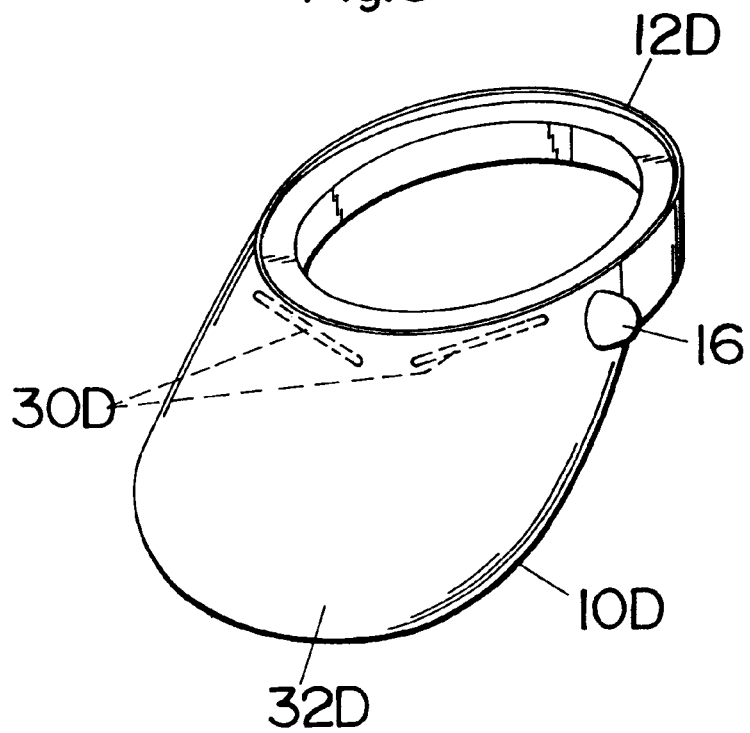

FIGS. 9 and 10 illustrate a portable illumination device in accordance with a third embodiment of the present invention. The device is identical in structure and operation to that of the second embodiment except that a light conductive panel 32D defining the bill of a visor 10D is curved and hinged at its rear end to the front of a headband 12D by means of a hinge 16. Thus, the light conductive panel 32D or the bill of the visor forms a surface illuminating unit 20D that can adjust its angular disposition relative to the face of the subject for effectively delivering the diffused light to the eyes. Like lamps 30D are accommodated in a rear portion of the bill.

Fourth Embodiment

Figure 11:
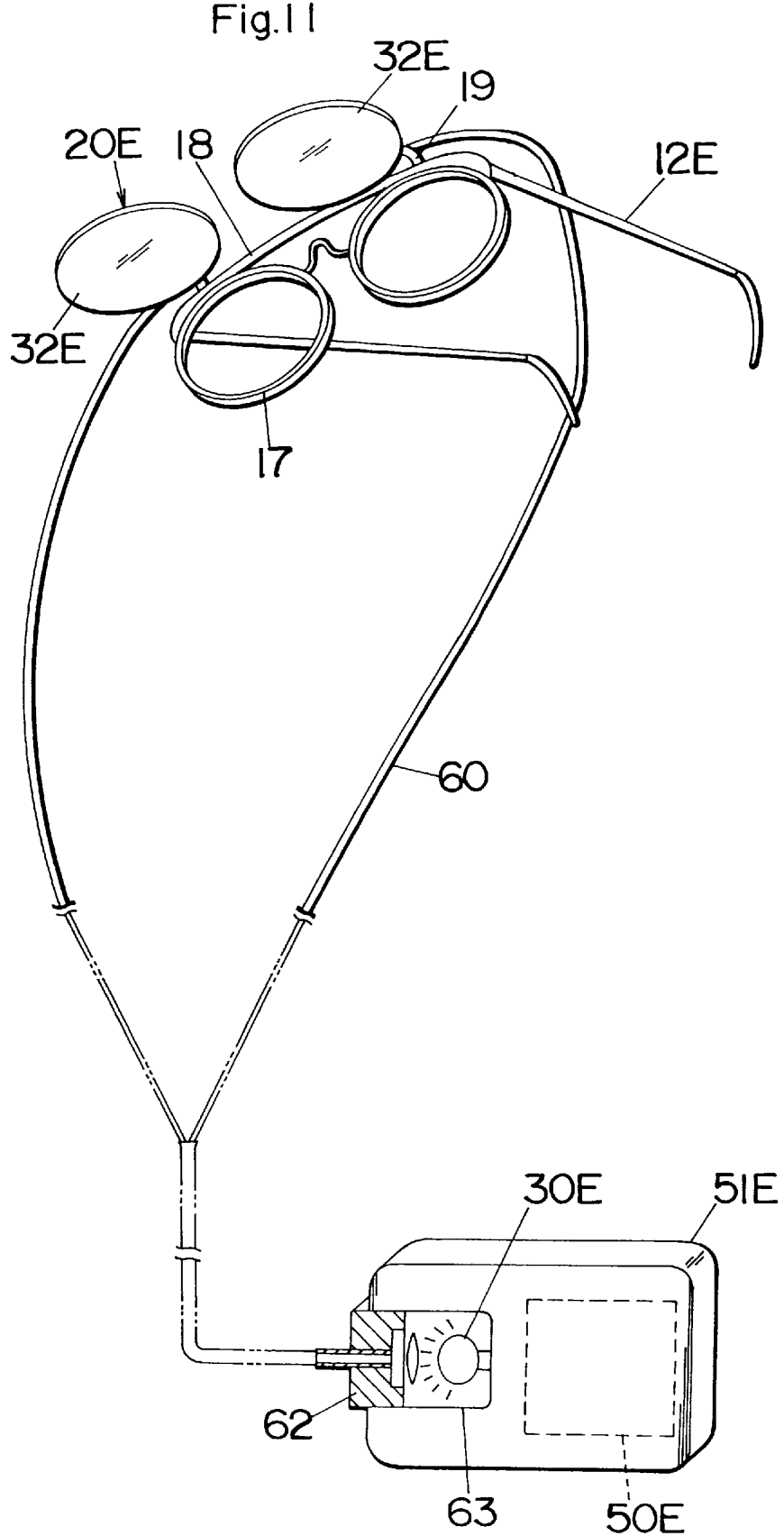
FIG. 11 is a perspective view of a portable illuminating device in accordance with a fourth embodiment of the present invention.
Figure 12:
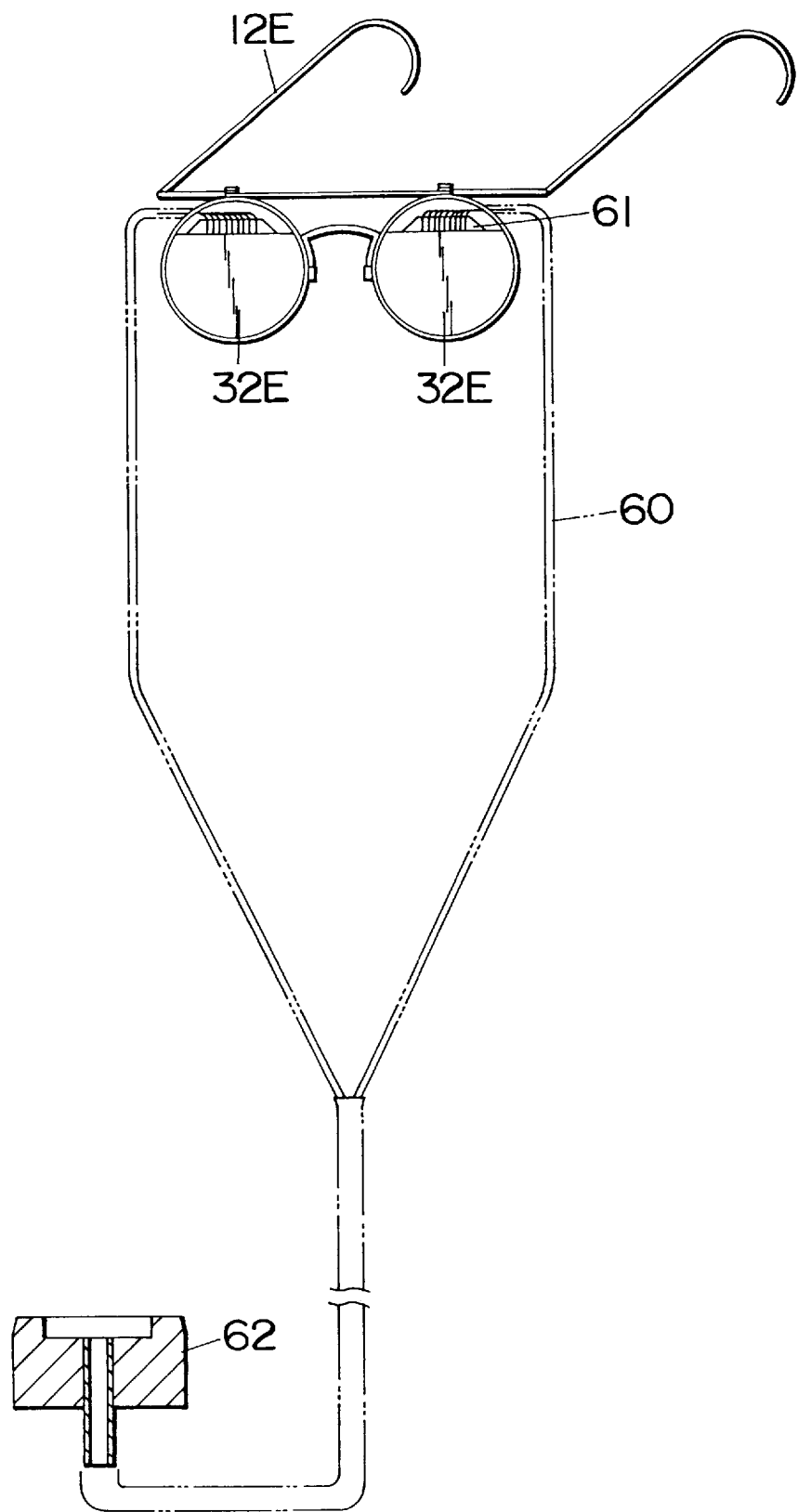
FIG. 12 is a schematic view of a major portion of the device of FIG. 11.

FIGS. 11 and 12 illustrate a portable illumination device in accordance with a fourth embodiment of the present invention. The device takes a form of spectacles 10E with temples 12E and bridge, and comprises, in addition to an eyeglass frame 17, a pair of light conductive flat plates 32E which defines a surface illuminating unit 20E. The pair of flat plates 32E is supported to a top bar 18 by means of a hinge 19 to be movable between a closed position for the light treatment with the plates 32E closed on the frame 17 and an open position for permitting the subject to make other daily activities, as well as to enable angular adjustment of the plates 32E with respect to the eyes of the subject wearing the spectacles 10E. The light conductive plate 32E is made of a transparent material as discussed previously and is covered with the like reflector on the front surface and with the like diffuser sheet on the rear surface for the purpose as discussed before. The plate 32E is connected through optical fibers 60 to a light source 30E accommodated in a separate controller housing 51E so as to receive the light therefrom. Formed at opposite ends of the bundle of the optical fibers 60 are respectively an output plug 61 and an input plug 62. As shown in FIGS. 13A and 13B, the output plug 61 carries the ends of optical fibers 60 in a parallel array and is detachably connected to a light inlet 33E of the panel 32E. The input plug 62 is detachably connected to a socket 63 in the controller housing 51E for optical connection to the light source 30E of an incandescent lamp through a converging lens. Although the input plug 62 is shown in FIGS. 12 and 13B to have the optical fibers 60 arranged in a spaced manner for easy recognition, the optical fibers 60 of 1 mm to 2 mm diameters are actually packed tightly for providing uniform light distribution to the plates 32E. The light source may be alternatively a halogen discharge lamp. A suitable optical filter may be utilized to alter color temperature the light from the light source and is disposed at the connection between the input plug 62 and the light source 30E. With the use of the optical fibers 60, the light source 30E can be separated from the surface illuminating unit 20E to make it lightweight enough to be worn without adding undue burden. The eyeglass frame 17 that is utilized for mounting the surface illuminating unit 20E may be of course be provided with suitable glass lenses.

Fifth Embodiment

FIGS. 14 and 15 illustrate a portable illumination device in accordance with a fifth embodiment of the present invention. The device comprises a tube 40 including light sources 30F, a light conductive panel 32F depending from the tube 40, and a headband 12F connected to opposite ends of the tube 40. The light sources 30F composed of incandescent lamps are disposed in the opposite ends of the tube 40 to emit the visible light inside of the tube. The tube 40 is made of a transparent material and, as shown in FIG. 16A, is covered on its internal surface with a reflection layer 41 and a prism layer 42 both having the like functions as the reflection sheet and prism sheet that are utilized in the first embodiment. Thus, the light from the light sources 30F undergoes a number of reflections by the reflection layer 41 as well as collections by the prism layer 42 to provide relatively uniform light intensity distribution along the length of the tube 40. As shown in FIGS. 15 and 16B, the reflection layer 41 is removed over a certain length at a portion opposed to the upper end of the light conductive panel 32D, and is replaced with a diffuser layer 43. Thus, the reflected light in the tube 40 is allowed to pass through the diffuser layer 43 thereby being diffused and directed into the light conductive panel 32F through a light inlet 33F at the upper end of the panel. The panel 32F is formed on its entire front surface with a combination of the like reflection sheet and diffuse reflection segments (not shown) as utilized in the first embodiment for reflecting the light entering the panel 32F towards a like diffuser sheet (not shown) formed on the entire rear surface of the panel 32F to constitutes a surface illuminating unit 20F for radiating the diffused visible light to the eyes of the subject wearing the device. The tube 40 is rotatably supported to the front end of the headband 12F such that the panel 32F fixed to the tube 40 can be held at any angular position relative to the face of the subject. Although not shown in the figures, a like controller circuit is provided in a separate housing to effect the like control as in the first embodiment.

Sixth Embodiment

Figure 17:
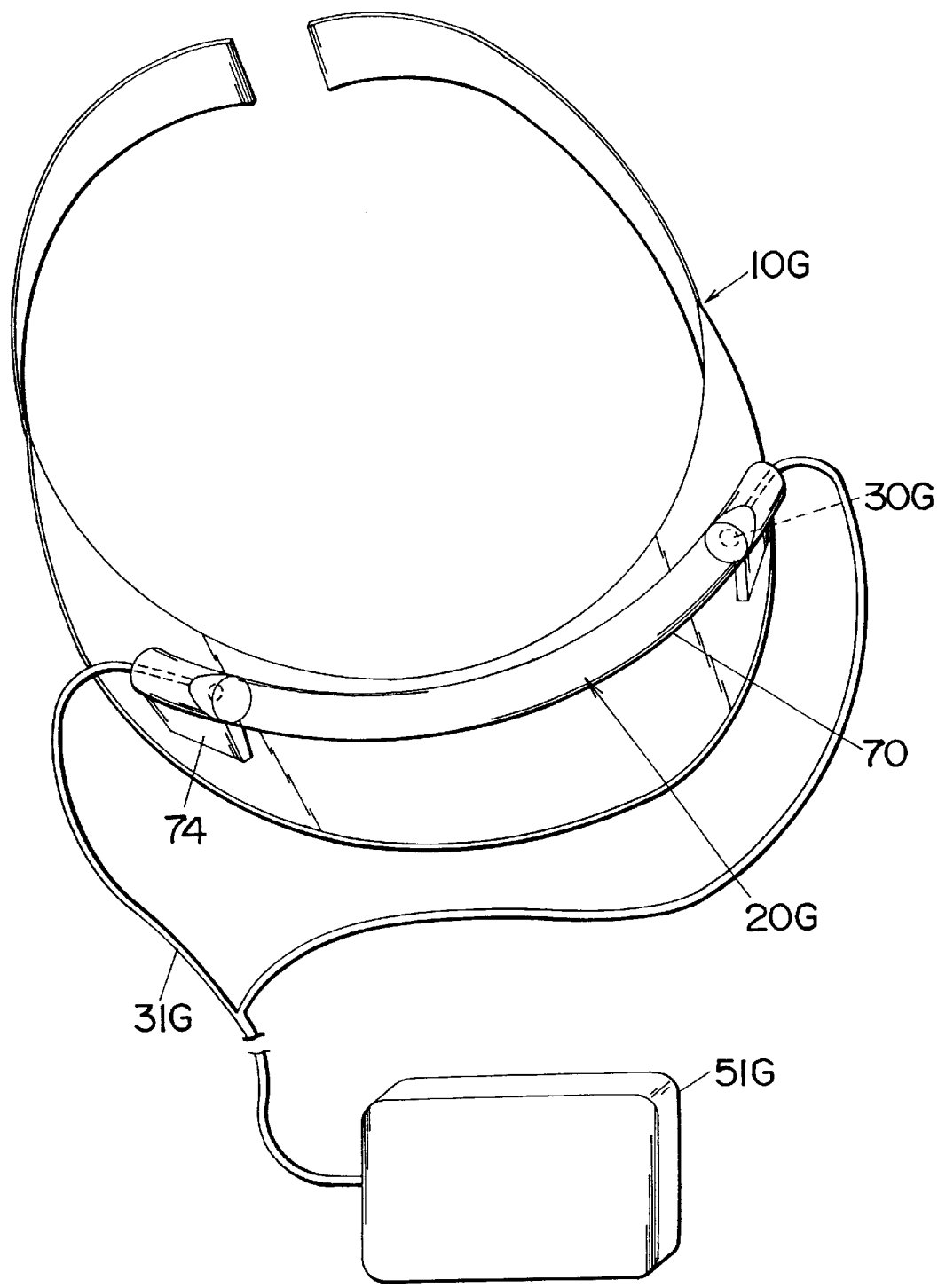
FIG. 17 is a schematic view of a portable illuminating device in accordance with a sixth embodiment of the present invention.

FIG. 17 illustrate a portable illumination device in accordance with a sixth embodiment of the present invention. The device comprises a surface illuminating unit 20G composed of a luminescent tube 70 supported to the bill of a visor 10G by brackets 74 in a somewhat curved fashion. The tube 70 is made of a transparent material such as acrylic resin and includes two separate light sources 30G of incandescent lamps in the opposite ends thereof. As shown in FIGS. 18A and 18B, the tube 70 is covered on about half circumference of the internal surface with a reflection layer 71 and a prism layer 72 both having the like functions as the reflection sheet and prism sheet that are utilized in the first embodiment and on the remaining half circumference with a diffuser layer 73 and the prism layer 72. The visible light from the lamps 30G undergoes a number of reflections and collections on and through the reflection layer 71 and the prism layer 72 within the tube 70 to give a substantially uniform light intensity distribution over the length of the tube. The light thus reflected and collected in the tube 70 is then allowed to pass through the prism layer 72 and the diffuser layer 73 to deliver the resulting visible diffused light to the eyes of the subject wearing the visor 10G. In this sense, the about half circumference of the tube 70 with the diffuser layer 73 defines surface light of source for the eyes. A reflector 35K is provided behind each of the lamps 30G/30K to direct the reflected light into the tube 70. A like controller housing 51G is provided separately from the visor 10G and includes a control circuit of the like configuration as shown in FIG. 4 to effect the like control. Extending from the controller housing 51G is a cable 31G for energizing the lamps 30G/30K in the tube 70.

Seventh Embodiment

FIG. 19 illustrates a portable illumination device in accordance with a seventh embodiment of the present invention which is similar to the sixth embodiment except that two ring-shaped luminescent tubes 70H are utilized to form a rim of spectacles 10H. The two light sources 30H of each tube 70H are spaced by an angle of about 180° within one ring and are disposed at connections respectively with the temple 12H and with a bridge 18H. In this embodiment, the half circumference of the tube 70H facing rearwardly thereof is provided with a like diffuser layer to define thereat the surface source of visible diffused light being delivered to the subject's eyes. Glass lenses may be mounted within the ring-shaped luminescent tubes 70H. In any case, the subject can receive the light treatment while being assured of the field of view for daily activities.

Eighth Embodiment

FIGS. 20 and 21 illustrate a portable illumination device in accordance with an eighth embodiment of the present invention. The device comprises a surface illuminating unit 20J secured to the bill of a visor and having a rectangular casing 21J for receiving an array of closely packed optical fibers 80 extending from a light source (not shown) within a separate controller housing 51J. The casing 21J includes a diffuser sheet 39J which covers the entire portion of the array of the optical fibers 80 located in the casing 21J. As shown in FIG. 21, each of the optical fibers 80 is stripped off its sheath 81 or cladding at a portion or portions facing the diffuser sheet 39J to define thereat a window or windows 82 through which the light guided through the optical fibers 80 is allowed to emerge outwardly thereof towards the diffuser sheet 39J, which in turn passes the light to radiate the visible diffused light. The window 82 of the single optical fiber 80 may be formed to be continuous over the entire width of the casing 21J or may be interrupted at a close interval. Further, the window 82 may extends circumferentially over an angle of 180°. In this case, the casing 21J is preferred to have a total internal reflection surface to reflect the leakage light towards the diffuser sheet 39J. A control circuit of the like functions as in the first embodiment is included in the controller housing 51J to give a controlled operation. A prism sheet of the type utilized in the first embodiment may be disposed on back of the diffuser sheet 39J.

Ninth Embodiment

Figure 22:
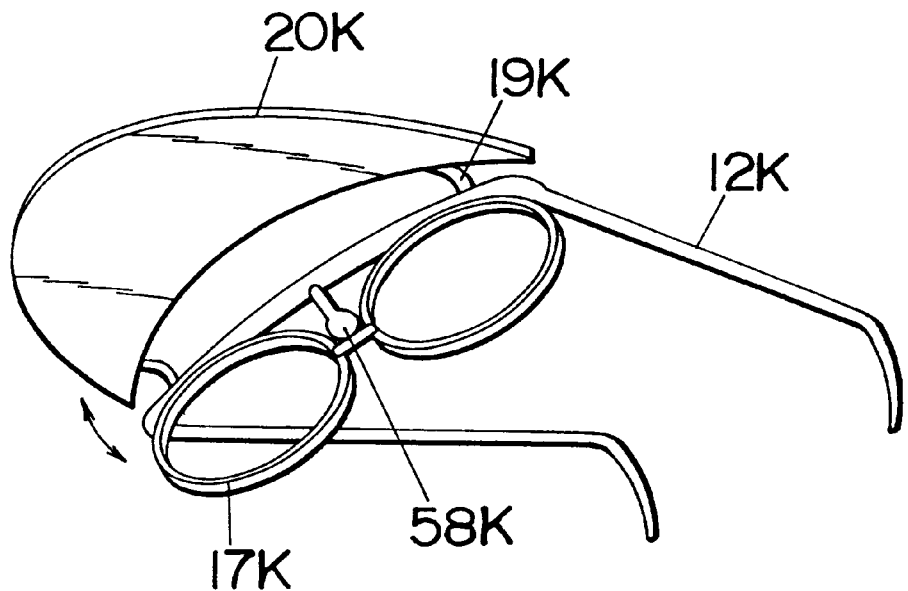
FIG. 22 is a perspective view of a portable illuminating device in accordance with a ninth embodiment of the present invention.
Figure 23:
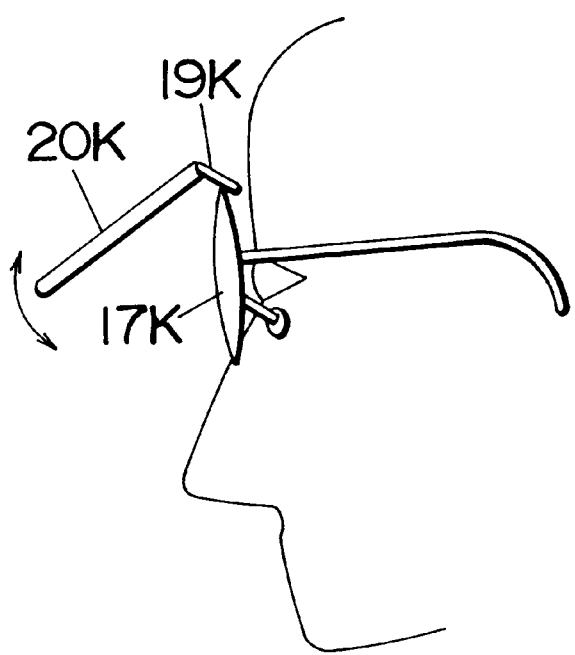
FIG. 23 is a schematic view of the device of FIG. 22 when worn on a subject's head.

FIGS. 22 and 23 illustrates a portable illumination device in accordance with a ninth embodiment of the present invention. The device takes the form of a pair of spectacles with a bill defined by a surface illuminating unit 20K. The bill or the illuminating unit 20K is connected to a top bar 90 of the spectacles through a hinge 19K to be capable of being closed and open in relation to the eyeglass frame 17K, and is therefore capable of being adjusted in its angular disposition relative to the subject's eyes. The surface illumination unit 20K is in the form of a self-illuminating panel such as an electroluminescent (EL) panel, plasma panel, or the like panel defining the surface source of light. The panel may be additionally provided with a diffuser sheet of the type utilized in the previous embodiments.

The device also includes a light sensor 58K for the same purpose as discussed with reference to the first embodiment. In this connection, the device also includes a control circuit of the like configuration and function as utilized in the first embodiment. The control circuit is preferably provided in a separate housing (not shown) together with a battery and associated components for energizing the panel 21K. The surface illuminating unit 20K may be a fluorescent lamp of a flat configuration which has an elongated discharge path extending in a spiral or zigzag pattern in a plane in a closely adjacent relation to give a uniform luminance distribution as intended.

Although the above embodiments discloses to mount the device on the human head by means of the visor or eyeglass frame, the device may be supported by any other means such as headgear, helmet, or the like and may be even supported to other part of the human body.

We claim:

1. A portable illumination device which is in use carried on a subject for modifying circadian rhythms of the subject, said device comprising:
    surface illuminating means having an effective surface region of at least 15 $cm^2$ for emitting a diffused visible light of reduced luminance variation, said diffused light giving an illuminance of at least 2000 LUX measured at an eye position of the subject; and
    mount means for mounting said surface illuminating means to a portion adjacent to eyes of the subject to direct said diffused light to a uniform visual field of each eye of the subject, wherein said surface illuminating means gives off said diffused light of which average luminance is set to be from 1,000 to 4,000 $cd/m^2$ and of which maximum luminance is less than 6,000 $cd/m^2$.

2. A portable illumination device which is in use carried on a subject for modifying circadian rhythms of the subject, said device comprising:
    surface illuminating means having an effective surface region of at least 15 $cm^2$ for emitting a diffused visible light of reduced luminance variation, said diffused light giving an illuminance of at least 2000 LUX measured at an eye position of the subject; and
    mount means for mounting said surface illuminating means to a portion adjacent to eyes of the subject to direct said diffused light to a uniform visual field of each eye of the subject, wherein a ratio of a maximum to minimum luminance appearing in said effective surface region is less than 2.5 and a difference in luminance between any two points spaced by 2 millimeter is less than 100 $cd/m^2$.

3. The illumination device as set forth in claim 1, wherein said surface illuminating means comprises a light conductive member formed with a light inlet for receiving a light from a separate light source and transmitting the light therethrough, said light conducting member being provided with diffusing means for diffusing said light emerging from said light conductive member to produce said diffused light directed to the eyes of the subject.

4. The illumination device as set forth in claim 3, wherein said light conductive member is made of a flexible material.

5. The illumination device as set forth in claim 3, wherein said light conductive member comprises a light permeable fluid or gel and a transparent envelop surrounding said light permeable fluid or gel.

6. The illumination device as set forth in claim 3, wherein said diffusing means comprises a diffuser plate and a prism sheet located between said flat diffuser plate and said light conductive member, said prism sheet being composed of a transparent sheet integrally molded with a plurality of discrete prism projections arranged in the surface of the sheet in order to orient the light proceeding outwardly of said light conductive member in a fixed direction towards said diffuser plate.

7. The illumination device as set forth in claim 3, wherein said light conductive member comprises a transparent plate with two opposite major surfaces and an end face defining said light inlet, one of said major surfaces being provided with said diffusing means, the other major surface being provided with a reflector for reflecting the light passing through said light inlet towards said diffusing means.

8. The illumination device as set forth in claim 7, wherein said reflector has a diffuse reflection surface for reflecting the light towards said diffusion means.

9. The illumination device as set forth in claim 8, wherein said diffuse reflection surface is formed to reflect an increasing amount of reflection at a portion remote from said light inlet.

10. The illumination device as set forth in claim 7, wherein said reflector has a total internal reflection surface for reflecting the light towards said diffusion means.

11. The illumination device as set forth in claim 7, wherein said light source emits the light including infrared component, and wherein said reflector is a dichroic mirror which passes the infrared component of said light while reflecting the light of the other visible light components toward said diffusing means.

12. The illumination device as set forth in claim 7, wherein said diffusion means comprises an opalescent sheet.

13. The illumination device as set forth in claim 7, wherein said diffusion means comprises a semi-transparent matted sheet.

14. The illumination device as set forth in claim 3, wherein said light conductive member is a transparent hollow cylinder having one end defining said light inlet, said cylinder being provided with said diffusing means around approximately half of its circumference and with a reflector around the remaining approximately half of the circumference for reflecting the light entering said cylinder towards said diffusing means.

15. The illumination device as set forth in claim 3, wherein said light conductive member comprises a plurality of parallel optical fibers with sheathes arranged in a row, one end of each said optical fiber being cooperative to form said light inlet, and said optical fibers being stripped of their sheathe at a portion adjacent to said diffusion means to give a window through which the light passing through said optical fiber is allowed to be directed outwardly towards and through said diffusion means.

16. The illumination device as set forth in claim 3, wherein said light conductive member has two opposed ends each defining said light inlet for receiving the light from each one of two said light sources.

17. The illumination device as set forth in claim 1, wherein said surface illuminating means comprises a self-illuminating panel.

18. The illuminating device as set forth in claim 1, wherein said mount means includes distance-adjusting means for adjusting the distance between said surface illuminating means and the eyes of the subject.

19. The illuminating device as set forth in claim 1, wherein said mount means includes angle-adjusting means for adjusting the angular relation between said surface illuminating means and the eyes of the subject.

20. The illuminating device as set forth in claim 1, further including:

control means for controlling to turn on and off said light, said control means being held in a housing which is provided separately from said surface illuminating means and is designed to be carried on said subject separately therefrom.

21. The illuminating device as set forth in claim 3, further including:

control means for controlling to turn on and off said light from said light source, said control means being held together with said light source in a housing which is provided separately from said light conductive member, said light conductive member being optically connected to said light source by means of a light guide member.

22. The illuminating device as set forth in claim 21, wherein said light guide member comprises an optical fiber.

23. The illuminating device as set forth in claim 1, further including:

control means for controlling to turn on and off said light, said control means includes a timer to turn on and off the light source respectively at selected start and end times.

24. The illuminating device as set forth in claim 1, further including:

dimming means for varying the intensity of the light emitted from said surface illumination means, said dimming means being controlled to increase the intensity of the light gradually in a non-linear relation with respect to time for a period of 5 min. to 30 min. from the start time of energizing the light and until the intensity of the light reaches a predetermined intensity.

25. The illumination device as set forth in claim 1, further including:

dimming means for varying the intensity of the light emitted from said surface illumination means; a light sensor disposed in the vicinity of the eyes to receive the diffused light from said surface illuminating means as well as from an environmental light reaching the eyes of the subject so as to provide an output indicative of the total amount of the lights actually delivered to the eyes of the subject over a predetermined period, and said dimming means being connected to said light sensor so as to adjust the intensity of the light from said light source in a feedback manner based upon the output from said light sensor to deliver an effective amount of the light to the eyes of the subject.

26. The illumination device as set forth in claim 24, further including:

an optical sensor mounted in the vicinity of the eyes to receive the diffused light from said surface illuminating means as well as from an environmental light directed to the eyes of the subject so as to provide an output indicative of the total amount of the diffused light actually delivered to the subject's eyes; and said control means being connected to receive the output from said optical sensor and determining an integrated illuminance of the light so as to stop generating said light irrespective of the control of said timer upon said integrated illuminance exceeding a predetermined level.

* * * * *